United States Patent [19]
Sugio et al.

[11] Patent Number: 4,751,022
[45] Date of Patent: Jun. 14, 1988

[54] HUMIDITY-SENSING COMPONENT COMPOSITION

[75] Inventors: Akitoshi Sugio, Ohmiya; Tadashi Shimomura, Nagareyama; Hidechika Wakabayashi, Matsudo; Osamu Kondo; Kazuharu Ogasawara, both of Tokyo; Chiharu Nishizawa, Matsudo, all of Japan

[73] Assignee: Mitsubishi Gas Chemical Company, Inc., Tokyo, Japan

[21] Appl. No.: 37,997

[22] Filed: Apr. 14, 1987

[30] Foreign Application Priority Data

Apr. 24, 1986 [JP] Japan ................... 61-93211
Apr. 24, 1986 [JP] Japan ................... 61-93212
Dec. 23, 1986 [JP] Japan ................... 61-305392

[51] Int. Cl.$^4$ ............................. H01B 1/06
[52] U.S. Cl. .................... 252/518; 252/519; 252/520; 252/521; 338/35
[58] Field of Search ............... 252/518, 519, 520, 521; 338/34, 35; 73/336, 336.5, 338, 73, 75, 27 R, 29; 264/61, 65, 66

[56] References Cited

U.S. PATENT DOCUMENTS

| | | | |
|---|---|---|---|
| 4,321,577 | 3/1982 | Carlson | 252/521 |
| 4,357,426 | 11/1982 | Murata | 252/520 |
| 4,373,391 | 2/1983 | Johnson | 338/35 |
| 4,462,930 | 7/1984 | Suzuki et al. | 252/521 |
| 4,464,647 | 8/1984 | Yokomizo et al. | 73/336 |
| 4,529,540 | 7/1985 | Uno et al. | 338/35 |
| 4,608,549 | 8/1986 | Fukui | 252/518 |

Primary Examiner—Josephine Barr
Attorney, Agent, or Firm—Foley & Lardner, Schwartz, Jeffery, Schwaab, Mack, Blumenthal & Evans

[57] ABSTRACT

A humidity-sensing component composition includes a metallic oxide and a chalcogen oxyacid salt represented by a general formula $A_xB_yO_z$ where A is one of an alkali metal and an alkaline earth metal, B is one of sulphur, selenium, and tellurium, O is oxygen, x is 1 to 2, y 1 to 5, and z 2 to 7. The chalcogen oxyacid salt is blended by an amount of 0.01 to 99.99 mol % in the metallic oxide with the sum of the metallic oxide and the chalcogen oxyacid salt as a reference. The metallic oxide and the chalcogen oxyacid salt are sintered under an atmosphere of molecular oxygen.

8 Claims, 4 Drawing Sheets

HUMIDITY-SENSING COMPONENT COMPOSITION

BACKGROUND OF THE INVENTION

1. Field of the Invention

The present invention relates to a humidity-sensing component composition which detects relative humidity as a change in the value of the electrical resistance.

2. Description of the Prior Art

Conventionally, materials known as humidity-sensing component compositions are:

(1) Materials using electrolytic quality salts such as lithium chloride;

(2) Materials utilizing organic polymer films such as polyamide or polyethylene films;

(3) Materials using metallic semiconductors such as selenium or germanium; and (4) Materials utilizing sintered bodies of metallic oxides such as titanium oxide, aluminium oxide, or stannic oxide.

Among these, the materials using sintered bodies of metallic oxides have the merit of being more stable chemically and physically than other humidity-sensing component compositions such as organic polymer films, and these can be said to be effective as humidity-sensing component compositions.

However, these sintered bodies of metallic oxides usually have the following types of drawbacks:

(1) The characteristic resistance value is high, and is not in the practical resistance value range. In regions of low humidity especially, the resistance of the humidity-sensing component composition abruptly becomes high, so the measurement of humidity in regions of low humidity is difficult.

(2) Dependence on temperature in the humidity-sensing characteristics is large, so temperature compensation is necessary.

(3) Hysteresis in the humidity-sensing characteristics is encountered when moisture is absorbed and released.

(4) Resistance to thermal shock is low, and the humidity-sensing characteristics deteriorate.

(5) Products of hydration are absorbed on and foul the surface of sintered bodies of metallic oxides so that the humidity-sensing characteristics deteriorate, making periodic heat cleaning necessary.

For these reasons, the development of a humidity-sensing component composition with high reliability has been greatly desired.

SUMMARY OF THE INVENTION

An object of the present invention is to provide, with due consideration to the drawbacks of such conventional materials, a reliable humidity-sensing component composition.

Another object of the present invention is to provide a humidity-sensing component composition in which the characteristic resistance value is low and is in the practical resistance value range.

Another object of the present invention is to provide a humidity-sensing component composition in which the dependence on temperature in the humidity-sensing characteristics is extremely small so that temperature compensation is unnecessary.

Another object of the present invention is to provide a humidity-sensing component composition in which hysteresis is almost absent in the humidity-sensing component characteristics when moisture is absorbed and released.

Another object of the present invention is to provide a humidity-sensing component composition which can withstand thermal shock.

Another object of the present invention is to provide a humidity-sensing component composition for which special heat cleaning is unnecessary.

Another object of the present invention is to provide a humidity-sensing component composition which exhibits good humidity-sensing characteristics in regions of low humidity, especially in regions of 40% RH and below.

With the above objects in view, the present invention resides in a humidity-sensing component composition including a metallic oxide and a chalcogen oxyacid salt represented by a general formula $A_xB_yO_z$ where A is one of an alkali metal and an alkaline earth metal, B is one of sulphur, selenium, and tellurium, O is oxygen, x is 1 to 2, y 1 to 5, and z 2 to 7, said chalcogen oxyacid salt being blended by an amount of 0.01 to 99.99 mol% in the metallic oxide with the sum of the metallic oxide and the chalcogen oxyacid salt as a reference, the metallic oxide and the chalcogen oxyacid salt being sintered under an atmosphere of molecular oxygen.

BRIEF DESCRIPTION OF THE DRAWINGS

The other objects, features, and advantages of the present invention will become more apparent from the following description of the preferred embodiments taken in conjunction with the accompanying drawings, in which:

FIG. 2 to FIG. 11 are graphs showing the characteristics of the humidity-sensing component composition of the present invention in which:

FIG. 2 and FIG. 3 show the humidity-sensing characteristics.

DETAILED DESCRIPTION OF THE PREFERRED EMBODIMENTS

A humidity-sensing component composition according to the present invention is now described in detail with reference to the drawings.

In the present invention, the metallic oxides used are materials which have humidity-sensing characteristics, and, if course, materials which are conventionally known as effective components of a humidity-sensing component composition are included. $MgO$, $TiO_2$, $ZrO_2$, $Nb_2O_5$, $TaO$, $Ta_2O_5$ $Cr_2O_3$, $MoO_3$, $WO_3$, $MnO_2$, $Mn_3O_4$, $FeO$, $Fe_2O_3$, $CoO$, $Co_2O_3$, $NiO$, $Ni_2O_3$, $Ni_3O_4$, $ZnO$, $Al_2O_3$, $Ga_2O_3$, $In_2O_3$, $Tl_2O_3$, $SiO_2$, $GeO_2$, $SnO$, $SnO_2$, $PbO$, $Sb_2O_3$, $Bi_2O_3$, and the like are given as examples of oxides, while $Mg_2Fe_2O_4$, $ZnFe_2O_4$, $MgAl_2O_4$, $MgCr_2O_3$, $ZnCr_2O_3$ (above, spinel), $3Al_2O_3.2SiO_2$ (Mullite), and the like are given as examples of compound oxides. Among these, $TiO_2$, $\gamma$-$Al_2O_3$, $ZnO$, $MgO$, $ZrO_2$, $NiO$, $MgAl_2O_2$ and the like are particularly desirable. Among the metallic oxides, those refined by thermal decomposition, such as metallic salts, metallic hydroxides, alkoxides, and the like are acceptable. Especially, in providing a humidity-sensing component composition for satisfactory measurement in low humidity regions of 40% RH or less, the use of a combination of metallic oxides such as titanium oxide, and cupric oxide or cuprous oxide is particularly desirable.

Chalcogen oxyacid salt is represented by the following general formula (I).

$$A_xB_yO_z \qquad (I)$$

wherein A is one of an alkali metal and an alkaline earth metal, B is one of sulphur, selenium, and tellurium, O is oxygen, x is 1 to 2, y 1 to 5, and z 2 to 7.

Specific examples of sulphur oxyacids are the sulphoxylates, sulphites, disulphites (metabisulphites), dithionites, disulphates (pyrosulphates), thiosulphates, and thionates. Specific examples of selenium oxyacids are the selenites and selenates. Specific examples of tellurium oxyacids are the tellurites and tellurates.

The ratios of metallic oxides and chalcogen oxyacid salts in the humidity-sensing component composition of the present convention are based on a reference value of the sum of the metallic oxide component and the chalcogen oxyacid salt component. The chalcogen oxyacid salt component will range from 0.01 to 99.99 mol%, with the desirable range being 0.1 to 99.9 mol%, especially less than 50 mol% in consideration of economy and characteristics. After blending each of the components for this humidity-sensing component composition, the sintered body obtained by means of suitable sintering conditions has an extremely improved humidity-sensing characteristic in comparison with a humidity-sensing component composition prepared from the metallic oxide only.

Particularly when providing a humidity-sensing component composition for satisfactory measurement in low humidity regions of 40% RH or less, a combination of metallic oxides such as titanium oxide, and cupric oxide or cuprous oxide, is used, with a range of 50 to 98 mol% for the titanium oxide, 1 to 40% for the cupric or cuprous oxide, and 1 to 10 mol% for the chalcogen oxyacid salt (alkali metal salt) being desirable. After each of the components are blended in these ranges, the humidity-sensing characteristics of the sintered body obtained under suitable sintering conditions give extremely good agreement with the characteristics obtained from the following equation (II), and an accurate expression of the humidity is obtained by means of a simple logarithmic conversion circuit. The measurement accuracy is considerably improved, especially in low humidity regions (40% RH or less).

$$H = \log K + a \qquad (II)$$

where H is the relative humidity, K is the impedance, and a is a constant.

The humidity-sensing component composition of the present invention can be manufactured in the following manner, using normal ceramics manufacturing technology.

First, after the required amount of each of the respective components has been weighed out, they are adequately blended in a ball mill, shaker mill, or the equivalent by means of a dry method or a wet method using a blended solvent such as water and methyl alcohol. Following this, the blended material is dried as required and calcinated at a suitable temperature, then crushed and prepared as the raw material powder. This raw material powder may be molded or acceptable is the process by which the raw material powder is kneaded together with a binder such as polyvinyl alcohol, polyethylene glycol or the like, then the kneaded material is prepared and dried, after which it is molded. This molded body is sintered under an atmosphere of molecular oxygen (usually air) to give a sintered body. This sintered body desirably has a porous structure, normally with a porosity of 10 to 55% and a pore diameter of $1\mu$ or less.

The humidity-sensing component composition of the present invention is usually obtained from a raw material powder with a particle diameter of 0.1 to $3\mu$, at a molding pressure of 50 to 1000 kg/cm², a sintering temperature of 500° to 1200° C. and a sintering time of 0.5 to 3 hours.

A humidity-sensing component can be constructed from the sintered body obtained in this manner by polishing as required, after which the electrodes are formed, utilizing a commonly used paste, such as gold paste, platinum paste, ruthenium oxide paste or the like. In addition, mass production methods can be used such as the thick film method, making cost reduction possible.

The humidity-sensing component composition of the present invention will now be explained with reference to the following embodiments.

Embodiment 1

Titanium oxide and sodium pyrosulphate ($Na_2S_2O_7$) were respectively weighed out in the mol ratios of 96.5% and 3.5% and mixed in a pot mill for 16 hours using the wet method. The resulting blended material was dried for four hours at 140° C., granulated, and prepared to give a raw material powder. This raw material powder was subjected to a pressure of 500 kg/cm² to mold a disc-shaped compacted body 12 mm in diameter and about 2 mm thick. This compacted body was sintered for 3 hours at 900° C., after which ruthenium oxide paste was printed by the seregraphy process in a comb shape onto one side of the sintered body and baked on at about 850° C.

Figure 1:
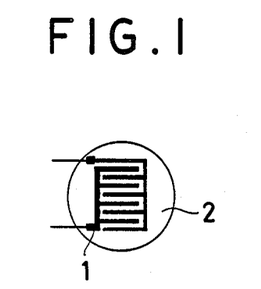
FIG. 1 is a front elevation showing one embodiment of the humidity-sensing component made from the humidity-sensing component composition of the present invention.

The structure of the humidity-sensing component manufactured in this manner is shown in FIG. 1. In FIG. 1, an electrode 1 and a humidity-sensing component 2 are shown.

Figure 2:
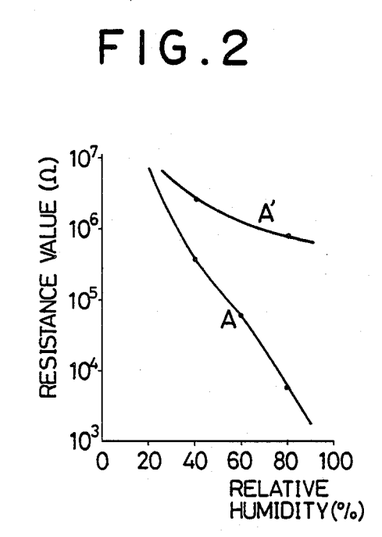

This humidity-sensing component was maintained in a constant temperature bath at an ambient temperature of 25° C., the relative humidity was varied from 20 to 100% and the change in its resistance value was investigated during this time. In FIG. 2, the resulting curve A is compared with curve A' which shows the change in resistance value of a humidity-sensing component in which the only component is titanium oxide. As clearly shown in FIG. 2, the resistance value of the humidity-sensing component composition of the present invention at an ambient temperature of 25° C. ranges from $1.04 \times 10^6$ ohms at a relative humidity of 30% to $4.5 \times 10^3$ ohms at a relative humidity of 80%, exhibiting over a wide humidity range a change in resistance value, which is known to be an extremely practical resistance value range.

Embodiment 2

Titanium oxide and barium selenite ($BaSeO_3$) were respectively weighted out in the mol ratios of 96.5% and 3.5% and mixed in a pot mill for 16 hours using the wet method. The resulting blended material was dried for four hours at 140° C., granulated, and prepared the raw material powder. This raw material powder was subjected to a pressure of 500 kg/cm² to form a disc-shaped compacted body 12 mm in diameter and about 2 mm thick. This compacted body was sintered for 3 hours at 1000° C., after which ruthenium oxide paste was screen printed in a comb shape onto one side of the sintered body and baked on at about 850° C.

This humidity-sensing component was maintained in a constant temperature bath with an ambient temperature of 25° C. or less, the relative humidity was varied from 20 to 100% and the change in its resistance value (humidity-sensing characteristics) was investigated during this time.

Figure 3:
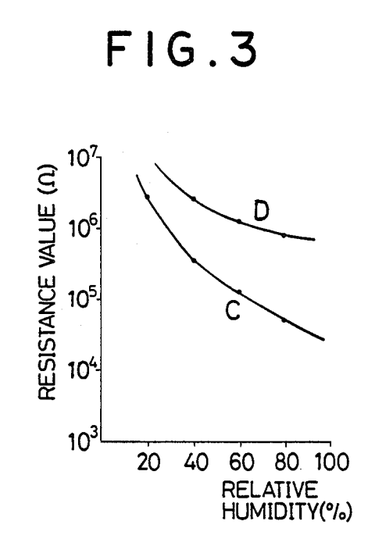

The result is shown in FIG. 3 in which the curve C shows the humidity-sensing characteristics which were obtained. For comparison, curve D shows the humidity-sensing characteristics of a humidity-sensing component made of only titanium oxide. As clearly shown in FIG. 3, the resistance value of the humidity-sensing component composition of the present invention at an ambient temperature of 25° C. ranges from $8.0 \times 10^5$ ohms at a relative humidity of 30% to $5.0 \times 10^4$ ohms at a relative humidity of 80%, exhibiting over a wide humidity range a change in resistance value, which is known to be an extremely practical resistance value range.

Embodiments 3 to 11

The compositions were sintered in the same way as in the Embodiment 1 and the humidity-sensing characteristics of the sintered bodies were investigated.

The results are given in Table 1. For comparison purposes, comparative example 1 showing the humidity-sensing characteristics of a sintered body made of only titanium oxide, is also included on the bottom line of the table. In Table 1, component (b) is a chalcogen oxyacid salt.

TABLE 1

| Embodiment | Component (b) | Composition (mol ratio), $TiO_2$/Component (b) | humidity sensing characteristics ($\Omega$) 30% RH | 80% RH |
|---|---|---|---|---|
| 3 | $Na_2S_2O_3$ | 96.5/3.5 | $4.2 \times 10^5$ | $2.8 \times 10^3$ |
| 4 | $Na_2S_2O_4$ | 96.5/3.5 | $2.9 \times 10^5$ | $3.6 \times 10^3$ |
| 5 | $Na_2S_2O_5$ | 96.5/3.5 | $1.8 \times 10^5$ | $5.8 \times 10^3$ |
| 6 | $Na_2S_2O_6$ | 96.5/3.5 | $5.0 \times 10^5$ | $2.3 \times 10^3$ |
| 7 | $Na_2SO_3$ | 96.5/3.5 | $2.6 \times 10^5$ | $8.5 \times 10^3$ |
| 8 | $Na_2SO_4$ | 96.5/3.5 | $1.2 \times 10^5$ | $6.4 \times 10^3$ |
| 9 | $Na_2TeO_3$ | 96.5/3.5 | $2.2 \times 10^5$ | $6.1 \times 10^3$ |
| 10 | $Na_2TeO_4$ | 96.5/3.5 | $1.7 \times 10^5$ | $2.4 \times 10^3$ |
| 11 | $Na_2SeO_4$ | 96.5/3.5 | $5.2 \times 10^5$ | $6.3 \times 10^2$ |
| Comparative Example 1 | $TiO_2$ | 100/0 | $7.2 \times 10^6$ | $8.1 \times 10^5$ |

Embodiments 12 and 13

The compositions were sintered in the same way as in the Embodiment 2 and the humidity-sensing characteristics of the sintered bodies were investigated.

The results are given in Table 2. For comparison purposes, comparative example 1 showing the humidity-sensing characteristics of a sintered body made of only titanium oxide, is also included on the bottom line of the table.

TABLE 2

| Embodiment | Component (b) | Composition (mol ratio), $TiO_2$/Component (b) | humidity sensing characteristics ($\Omega$) 30% RH | 80% RH |
|---|---|---|---|---|
| 12 | $BaSO_4$ | 96.5/3.5 | $3.0 \times 10^6$ | $9.0 \times 10^4$ |
| 13 | $BaTeO_3$ | 96.5/3.5 | $1.5 \times 10^6$ | $7.0 \times 10^4$ |
| Comparative Example 1 | $TiO_2$ | 100/0 | $7.2 \times 10^6$ | $8.1 \times 10^5$ |

Embodiment 14

In the same way as in the Embodiment 1, a composition containing titanium oxide and potassium selenite ($K_2SeO_3$) in the mol% of 96.5% and 3.5% respectively was sintered, and the humidity-sensing characteristics of the sintered body were investigated. The results are given in Table 3.

TABLE 3

| Embodiment | Component (b) | Composition (mol ratio), $TiO_2$/Component (b) | humidity sensing characteristics ($\Omega$) 30% RH | 80% RH |
|---|---|---|---|---|
| 14 | $K_2SeO_3$ | 96.5/3.5 | $1.4 \times 10^5$ | $7.5 \times 10^3$ |

Embodiment 15

In the same way as in the Embodiment 2, a composition containing titanium oxide and calcium tellurite ($CaTeO_3$) in the mol% of 96.5% and 3.5% respectively was sintered, and the humidity-sensing characteristics of the sintered body were investigated. The results are given in Table 4.

TABLE 4

| Embodiment | Component (b) | Composition (mol ratio), $TiO_2$/Component (b) | humidity sensing characteristics ($\Omega$) 30% RH | 80% RH |
|---|---|---|---|---|
| 15 | $CaTeO_3$ | 96.5/3.5 | $9.2 \times 10^5$ | $5.5 \times 10^4$ |
| Comparative Example 1 | $TiO_2$ | 100/0 | $7.2 \times 10^6$ | $8.1 \times 10^5$ |

Embodiments 16 to 28

The compositions were sintered in the same way as in the Embodiment 1 and the humidity-sensing characteristics of the sintered bodies were investigated.

The results are given in Table 5. In Table 5, component (a) is a metallic oxide.

TABLE 5

| Embodiment | Component (a) | Composition (mol ratio), Component (a)/Na$_2$TeO$_3$ | humidity sensing characteristics ($\Omega$) 30% RH | 80% RH |
|---|---|---|---|---|
| 16 | ZnO | 96.5/3.5 | $5.0 \times 10^5$ | $1.5 \times 10^4$ |
| 17 | MgO | 96.5/3.5 | $5.1 \times 10^5$ | $1.4 \times 10^4$ |
| 18 | ZrO | 96.5/3.5 | $4.8 \times 10^5$ | $1.3 \times 10^4$ |
| 19 | $\gamma$-Al$_2$O$_3$ | 96.5/3.5 | $8.4 \times 10^5$ | $1.7 \times 10^4$ |
| 20 | NiO | 96.5/3.5 | $1.3 \times 10^6$ | $3.2 \times 10^4$ |
| 21 | Y$_2$O$_3$ | 96.5/3.5 | $1.6 \times 10^5$ | $1.0 \times 10^4$ |
| 22 | WO$_3$ | 96.5/3.5 | $5.6 \times 10^5$ | $3.3 \times 10^5$ |
| 23 | MnO$_2$ | 96.5/3.5 | $1.6 \times 10^6$ | $6.6 \times 10^4$ |
| 24 | Fe$_2$O$_3$ | 96.5/3.5 | $2.4 \times 10^5$ | $1.2 \times 10^4$ |
| 25 | SiO$_2$ | 96.5/3.5 | $2.5 \times 10^6$ | $2.6 \times 10^4$ |
| 26 | SnO$_2$ | 96.5/3.5 | $4.9 \times 10^4$ | $2.3 \times 10^3$ |
| 27 | Sb$_2$O$_3$ | 96.5/3.5 | $6.7 \times 10^5$ | $8.4 \times 10^4$ |
| 28 | MgAl$_2$O$_4$ | 96.5/3.5 | $4.0 \times 10^5$ | $1.2 \times 10^4$ |

Embodiments 29 to 41

The compositions were sintered in the same way as in the Embodiment 2 and the humidity-sensing characteristics of the sintered bodies were investigated. The results are given in Table 6.

TABLE 6

| Embodiment | Component (a) | Composition (mol ratio), Component (a)/BaSeO$_3$ | humidity sensing characteristics ($\Omega$) 30% RH | 80% RH |
|---|---|---|---|---|
| 29 | ZnO | 96.5/3.5 | $9.0 \times 10^5$ | $7.1 \times 10^4$ |
| 30 | MgO | 96.5/3.5 | $9.3 \times 10^5$ | $7.0 \times 10^4$ |
| 31 | ZrO$_2$ | 96.5/3.5 | $8.2 \times 10^5$ | $6.5 \times 10^4$ |
| 32 | $\gamma$-Al$_2$O$_3$ | 96.5/3.5 | $1.0 \times 10^6$ | $7.3 \times 10^4$ |
| 33 | NiO | 96.5/3.5 | $2.2 \times 10^6$ | $9.1 \times 10^4$ |
| 34 | Y$_2$O$_3$ | 96.5/3.5 | $6.6 \times 10^5$ | $6.0 \times 10^4$ |
| 35 | WO$_3$ | 96.5/3.5 | $1.2 \times 10^6$ | $8.4 \times 10^5$ |
| 36 | MnO$_2$ | 96.5/3.5 | $6.6 \times 10^6$ | $1.2 \times 10^5$ |
| 37 | Fe$_2$O$_3$ | 96.5/3.5 | $7.5 \times 10^5$ | $6.2 \times 10^4$ |
| 38 | SiO$_2$ | 96.5/3.5 | $7.5 \times 10^6$ | $7.6 \times 10^4$ |
| 39 | SnO$_2$ | 96.5/3.5 | $9.9 \times 10^4$ | $7.3 \times 10^3$ |
| 40 | Sb$_2$O$_3$ | 96.5/3.5 | $1.4 \times 10^6$ | $1.8 \times 10^5$ |
| 41 | MgAl$_2$O$_4$ | 96.5/3.5 | $9.0 \times 10^5$ | $6.2 \times 10^4$ |

Embodiments 42 to 44

The compositions were sintered in the same way as in the Embodiment 1 and the humidity-sensing characteristics of the sintered bodies were investigated. The results are given in Table 7. In Table 7, the results for Embodiment 9 are also included.

TABLE 7

| Embodiment | Components (mol %) TiO$_2$ | Na$_2$TeO$_3$ | humidity-sensing characteristics ($\Omega$) 30% RH | 80% RH |
|---|---|---|---|---|
| 42 | 99.9 | 0.1 | $7.2 \times 10^5$ | $3.0 \times 10^4$ |
| 9 | 96.5 | 3.5 | $2.2 \times 10^5$ | $6.1 \times 10^3$ |
| 43 | 50.0 | 50.0 | $5.0 \times 10^5$ | $1.5 \times 10^3$ |
| 44 | 0.1 | 99.9 | $4.0 \times 10^5$ | $1.0 \times 10^3$ |

Embodiments 45 to 47

The compositions were sintered in the same way as in the Embodiment 2 and the humidity-sensing characteristics of the sintered bodies were investigated. The results are given in Table 8. In Table 8, the results of Embodiment 2 are also included.

TABLE 8

| Embodiment | Components (mol %) TiO$_2$ | BaSeO$_3$ | humidity-sensing characteristics ($\Omega$) 30% RH | 80% RH |
|---|---|---|---|---|
| 45 | 99.9 | 0.1 | $9.2 \times 10^5$ | $6.6 \times 10^4$ |
| 2 | 96.5 | 3.5 | $8.0 \times 10^5$ | $5.0 \times 10^4$ |
| 46 | 50.0 | 50.0 | $7.0 \times 10^5$ | $3.7 \times 10^4$ |
| 47 | 0.1 | 99.9 | $3.5 \times 10^5$ | $1.7 \times 10^4$ |

Embodiment 48

The sintered body of the humidity-sensing component composition used in the Embodiment 9 was maintained at ambient temperatures of 25° C., 40° C., 60° C., and 80° C., the relative humidity was changed from 20 to 100% and its humidity-sensing characteristics were investigated during this time. The results are shown in FIG. 4.

Figure 4:
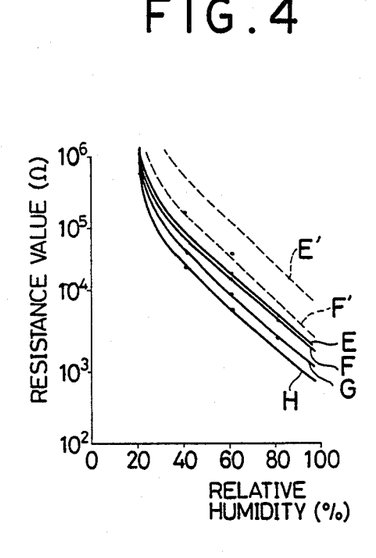
FIG. 4 and FIG. 5 show the relationship between temperature and the humidity-sensing characteristics.

In FIG. 4 the curves E, F, G, and H show the humidity-sensing characteristics at ambient temperatures of 25°, 40°, 60°, and 80° C. respectively. In addition, the humidity-sensing characteristics of a conventional humidity-sensing component composition are shown as dotted line curves in FIG. 4 for comparison purposes. The dotted line curves labelled E' and F' are the humidity-sensing characteristics at ambient temperatures of 25° C. and 40° C. respectively. As clearly shown in FIG. 4, at ambient temperatures from 25° C. to 40° C. the temperature dependency is extremely small so it can be understood that there is no necessity for temperature compensation. Also, in the humidity-sensing component composition of the present invention, the total change in the humidity-sensing characteristics in the ambient temperature range of 25° to 80° C. corresponds to the change in the humidity-sensing characteristics of the conventional composition at ambient temperatures of 25° C. to 40° C. Compared to the conventional composition, it is understood that the temperature characteristics of the humidity-sensing component composition of the present invention are greatly improved.

Embodiment 49

The sintered body of the humidity-sensing component composition used in the Embodiment 2 was maintained at ambient temperatures of 25° C., 40° C., 60° C., and 80° C., the relative humidity was changed from 20 to 100%, and its humidity-sensing characteristics were investigated during this time. The results are shown in FIG. 5.

Figure 5:
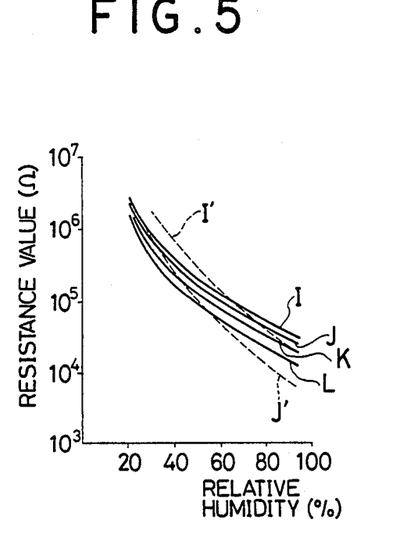

In FIG. 5 the curves I, J, K, and L show the humidity-sensing characteristics at ambient temperatures of 25°, 40°, 60°, and 80° C. respectively. In addition, the humidity-sensing characteristics of a conventional humidity-sensing component composition are shown as dotted line curves in FIG. 5 for comparison purposes. The dotted line curves labelled I' and J' are the humidity-sensing characteristics at ambient temperatures of 25° C. and 40° C. respectively. As clearly shown in FIG. 5, the temperature dependency at ambient temperatures from 25° C. to 40° C. is extremely small so it can be understood that there is no necessity for temperature compensation. Also, in the humidity-sensing component composition of the present invention, the total change in the humidity-sensing characteristics in the ambient temperature range of 25° to 80° C. corresponds to the change in the humidity-sensing characteristics of the conventional composition at ambient temperatures of 25° C. to 40° C. Compared to the conventional composition, it is understood that the temperature characteristics of the humidity-sensing component composition of the present invention are greatly improved.

Embodiment 50

In the same way as in the Embodiment 1, a composition containing titanium oxide and potassium selenite ($K_2SeO_3$) in the mol% ratios of 89.5% and 10.5% respectively was sintered.

After the sintered bodies obtained in this manner had been held in a relative humidity of 98% at an ambient temperature of 25° C. for 24 hours, the hysteresis in the humidity-sensing characteristics was investigated at the above ambient temperatures in a range of relative humidities from 20% to 80%. Also, in the same way as outlined above, the hysteresis in the humidity-sensing characteristics of the sintered body of the composition of the Embodiment 9 was investigated.

Figure 6:
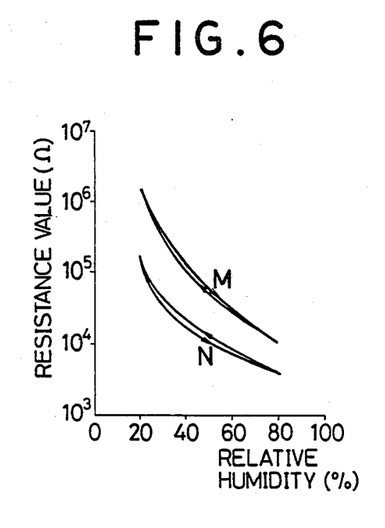
FIG. 6 and FIG. 7 show the hysteresis in the humidity-sensing characteristics after the composition was held under conditions of high humidity.

The results are shown in FIG. 6. The curves M and N in FIG. 6 show the results of the Embodiments 9 and 50 respectively. As is clearly shown in FIG. 6, the hysteresis in the humidity-sensing characteristics of the sintered body of these compositions is about ±3% RH. It is therefore understood that the amount of hysteresis is extremely small, even when the sintered body component is held for 24 hours at a relative humidity of 98%.

Embodiment 51

The sintered bodies of the humidity-sensing component compositions used in the Embodiments 2 and 13 were maintained at an ambient temperature of 25° C. and an ambient relative humidity of 98% for 24 hours, after which, at the same ambient temperature the hysteresis in the humidity-sensing characteristics was investigated over a relative humidity range of 20 to 80%.

Figure 7:
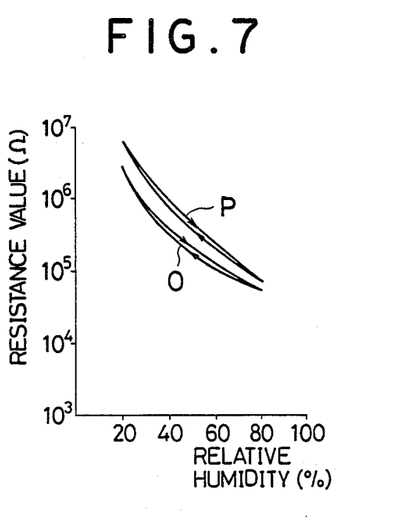

The results are shown in FIG. 7. The curves O and P in FIG. 7 show the results of the Embodiments 2 and 13 respectively. As clearly shown in FIG. 7, the hysteresis for the humidity-sensing characteristics of the sintered body of the composition is within ±2% RH. It is therefore understood that the amount of hysteresis is extremely small, even when the sintered body component is held for 24 hours at a relative humidity of 98%.

Embodiment 52

The humidity-sensing component composition of the Embodiment 9 was subjected to 50 cycles of a thermal shock test as one cycle of 30 minutes at an ambient temperature of 85° C., and thereafter 30 minutes at an ambient temperature of −25° C. The humidity-sensing characteristics of this humidity-sensing component composition were investigated both before and after the thermal shock tests in the same way as for Embodiment 1.

Figure 8:
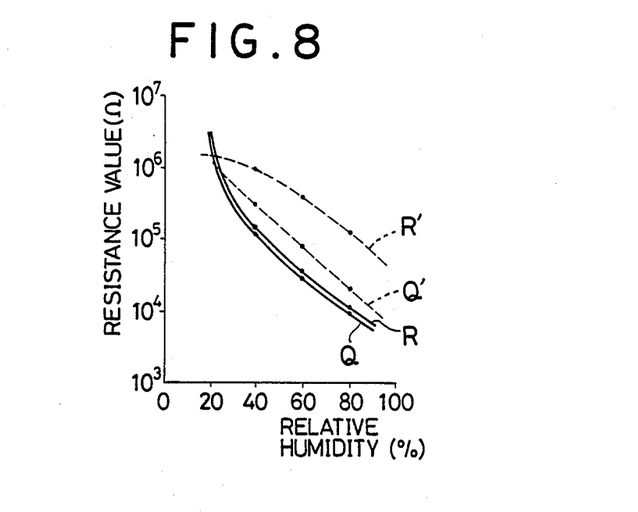
FIG. 8 and FIG. 9 show the humidity-sensing characteristics before and after the composition was subjected to a thermal shock test.

The results are shown in FIG. 8. In FIG. 8 the curve Q shows the humidity-sensing characteristics before the tests, while the curve R shows the humidity-sensing characteristics after the tests. For purposes of comparison, the humidity-sensing characteristics were also investigated for a conventional humidity-sensing component composition both before and after the identical thermal shock tests and are shown by curves Q' and R' respectively. As clearly shown in FIG. 8, the changes in the humidity-sensing characteristics of this embodiment before and after the thermal shock tests is within 3%. It is therefore understood that compared to the conventional humidity-sensing component composition the composition in this embodiment has an extremely high resistance to thermal shock.

Embodiment 53

The component sintered body used in the Embodiment 13 was subjected to 50 cycles of a thermal shock test as one cycle of 30 minutes at an ambient temperature of 85° C., and thereafter 30 minutes at an ambient temperature of −25° C. The humidity-sensing characteristics of this humidity-sensing component composition were investigated both before and after the thermal shock tests in the same way as for Embodiment 2.

Figure 9:
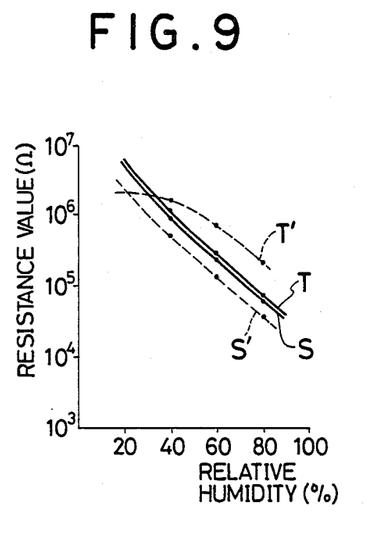

The results are shown in FIG. 9. In FIG. 9 the curve S shows the humidity-sensing characteristics before the tests, while the curve T shows the humidity-sensing characteristics after the tests. For purposes of comparison, the humidity-sensing characteristics were also investigated for a conventional humidity-sensing component composition both before and after the identical thermal shock tests and are shown by curves S' and T' respectively. As clearly shown in FIG. 9, the change in the humidity-sensing characteristics of this embodiment before and after the thermal shock tests is within 3%. It is therefore understood that compared to the conventional humidity-sensing component composition the composition in this embodiment has an extremely high resistance to thermal shock.

Embodiment 54

The humidity-sensing component composition of the Embodiment 50 was held in an environment of an ambient temperature of 85° C. and a relative humidity of 80% for one month. The humidity-sensing characteristics of this humidity-sensing component composition were investigated both before and after this holding test in the same way as for Embodiment 1.

The results are shown in Table 9. As clearly shown in Table 9, the humidity-sensing characteristics of this embodiment show an extremely small amount of change even when held for a prolonged period of time under a severe environment of high temperature and high humidity. Accordingly, it is understood that under normal environmental conditions this humidity-sensing component composition can be used for a long time without requiring special heat cleaning.

TABLE 9

| Relative humidity | humidity-sensing characteristics (Ω) | |
|---|---|---|
| | 30% RH | 80% RH |
| Initial humidity-sensing characteristics | 7.0 × 10⁵ | 6.5 × 10³ |
| Humidity-sensing characteristics after test | 8.2 × 10⁵ | 5.8 × 10³ |

Embodiment 55

The sintered bodies of the humidity-sensing component compositions used in the Embodiments 2 and 13 were immersed in distilled water for one month at a temperature of 25° C., after which they were dried under a current of air. The humidity-sensing characteristics were investigated in the same way as for embodiment 2 both before and after these tests.

Figure 10:
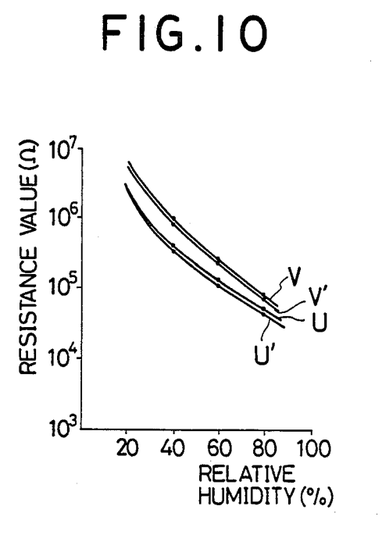
FIG. 10 shows the humidity-sensing characteristics before and after the composition was subjected to a water resistance test.

The results are shown in FIG. 10. The curves U and U' show the humidity-sensing characteristics of the sintered body of the Embodiment 2, before and after the test respectively, while the curves V and V' show the humidity-sensing characteristics of the sintered body of the Embodiment 13, before and after the test respectively.

As clearly shown in FIG. 10, the humidity-sensing characteristics of these embodiments show almost no change after the test in comparison with the characteristics before the test. Accordingly, it is understood that even under an environment of severe water conditions there is no concern about deterioration of the humidity-sensing characteristics of these humidity-sensing component compositions, so that they can be used for a long time without requiring special heat cleaning.

Embodiment 56

Titanium oxide, cupric oxide, and sodium tellurite ($Na_2TeO_3$) were respectively weighed out in the mol ratios of 82%, 15%, and 3% and mixed in a pot mill for 16 hours using the wet method. The resulting blended material was dried for four hours at 140° C., granulated, and prepared the raw material powder. This raw material powder was subjected to a pressure of 500 kg/cm² to mold a disc-shaped compacted body 7 mm in diameter and about 0.7 mm thick. This compacted body was sintered for 3 hours at 900° C., after which ruthenium oxide paste was printed by the seregraphy process in a comb shape onto one side of the sintered body and baked on at about 850° C.

The humidity-sensing component manufactured in this manner was maintained in a constant temperature bath at an ambient temperature of 25° C. and the relative humidity was changed from 5% to 100%. The change in the resistance values was investigated during this time. The results are given in Table 10. For comparison purposes, the humidity-sensing characteristics of a sintered body comprising titanium oxide and sodium tellurite in the mol ratios of 96.5% and 3.5% respectively are also included in Table 10 as Comparative Example 2.

TABLE 10

| Embodiment | Components (mol %) | | | Humidity-sensing characterisitics (Ω) | | |
|---|---|---|---|---|---|---|
| | $TiO_2$ | $Na_2TeO_3$ | $Cu_2O$ | 10% RH | 30% RH | 80% RH |
| 56 | 82 | 3 | 15 | $4.0 \times 10^5$ | $1.07 \times 10^5$ | $4.1 \times 10^3$ |
| Comparative Example 2 | 97 | 3 | 0 | $2.5 \times 10^7$ | $2.2 \times 10^5$ | $6.1 \times 10^3$ |

Embodiment 57

Cuprous oxide was substituted for cupric oxide in the Embodiment 56, a sintered body was manufactured in the same way as in the Embodiment 56, and the humidity-sensing characteristics of the sintered body were investigated. The results are given in Table 11.

TABLE 11

| Embodiment | Components (mol %) | | | Humidity-sensing characterisitics (Ω) | | |
|---|---|---|---|---|---|---|
| | $TiO_2$ | $Na_2TeO_3$ | $CuO$ | 10% RH | 30% RH | 80% RH |
| 57 | 87 | 3 | 10 | $4.3 \times 10^5$ | $1.15 \times 10^5$ | $4.3 \times 10^3$ |

Embodiment 58

Titanium oxide, cuprous oxide, and potassium selenite ($K_2SeO_3$) were respectively weighed out in the mol ratios of 82%, 15%, and 3% and subjected to the same blending, molding, and sintering processes as in the Embodiment 56. The sintered body obtained in this manner was held for 24 hours at an ambient temperature of 25° C. and a relative humidity of 98%, after which, at the same ambient temperature, the relative humidity was varied in the range of 20% to 80% and the hysteresis in the humidity-sensing characteristics was investigated. The results are shown in FIG. 11.

Figure 11:
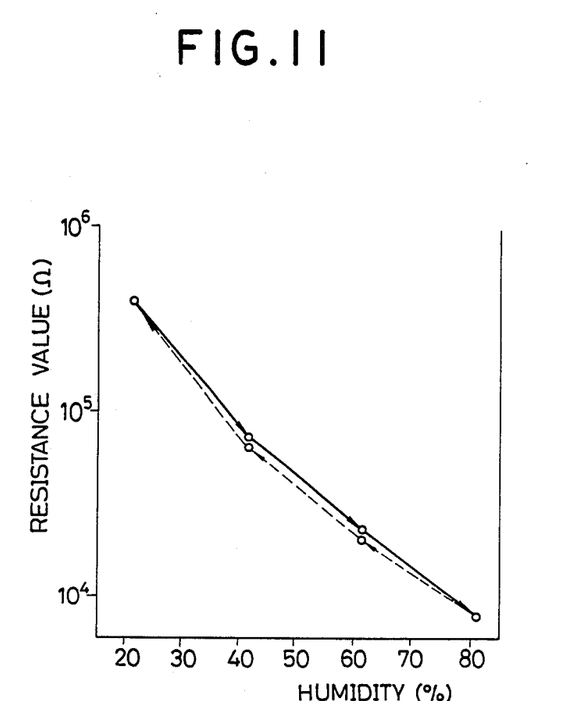
FIG. 11 shows the hysteresis in the humidity-sensing characteristics after the composition was held under conditions of high humidity.

As is clearly shown in FIG. 11, the hysteresis for the humidity-sensing characteristics of the sintered body of this composition is within ±2% RH. It is therefore understood that the amount of hysteresis is extremely small, even when the sintered body component is held for 24 hours at a relative humidity of 98%.

In the above manner, by means of the present invention it is possible to provide a humidity-sensing component composition in which, in comparison with the conventional humidity-sensing component compositions, the characteristic resistance value is low and is in the practical resistance value range; the dependence on temperature in the humidity-sensing characteristics is extremely small so that temperature compensation is unnecessary; hysteresis is almost absent in the humidity-sensing component characteristics when moisture is absorbed and released. Also, this composition can withstand thermal shock and special heat cleaning is unnecessary.

In addition, when an alkaline earth metal salt is used as a chalcogen oxyacid salt, it is possible to provide a humidity-sensing component composition with superior water resistance.

Further, when an alkali metal salt is used as a chalcogen oxyacid salt and when titanium oxide and either cupric oxide or cuprous oxide as a metallic oxide are used together, it is possible to provide a reliable humidity-sensing component composition in which, in comparison with the conventional humidity-sensing component compositions, the characteristic resistance value is low and is in the practical resistance value range. This composition also exhibits good humidity-sensing characteristics in regions of low humidity, especially in regions below 40% RH; hysteresis is almost absent in the humidity-sensing component characteristics when moisture is absorbed and released; and special heat cleaning is unnecessary.

What is claimed is:

1. A humidity-sensing component composition consisting essentially of a metallic oxide selected from the group consisting of oxides and compound oxides of titanium, zinc, magnesium, zirconium, aluminum, nickel, yttrium, tungsten, manganese, iron, silicon, tin and antimony, and a chalcogen oxyacid salt represented by the general formula $A_xB_yO_z$ where A is selected from the group consisting of sodium, potassium, barium and calcium, B is selected from the group consisting of sulphur, selenium, and tellurium, O is oxygen, x is 1 to 2, y is 1 to 5, and z is 2 to 7, said chalcogen oxyacid salt being blended in an amount of 0.01 to 99.99 mol% in the metallic oxide with reference to the sum of the metallic oxide and the chalcogen oxyacid salt being 100 mol%, the metallic oxide and the chalcogen oxyacid salt being sintered at a temperature in the range from 500° to 1200° C. under an atmosphere of molecular oxygen.

2. The humidity-sensing component composition as claimed in claim 1, wherein the chalcogen oxyacid salt is blended in an amount of 0.1 to 99.9 mol% in the metallic oxide with reference to the sum of the metallic oxide and the chalcogen oxyacid salt being 100 mol%.

3. The humidity-sensing component composition as claimed in claim 1 wherein the chalcogen oxyacid salt is an alkali metal salt.

4. The humidity-sensing component composition as claimed in claim 1 wherein the chalcogen oxyacid salt is a tellurium salt.

5. The humidity-sensing component composition as claimed in claim 1, wherein the metallic oxide is at least one oxide selected from the group consisting of $TiO_2$, $\gamma$-$Al_2O_3$, ZnO, MgO, $ZrO_2$, NiO, and $MgAl_2O_4$.

6. The humidity-sensing component composition as claimed in claim 1 wherein the metallic oxide is $TiO_2$.

7. The humidity-sensing component composition as claimed in claim 1, wherein the chalcogen oxyacid salt is an alkali metal salt and the metallic oxide is titanium oxide, and further comprising up to 40 mole%, based on the total composition, of a copper oxide selected from the group consisting of cupric oxide and cuprous oxide.

8. The humidity-sensing component composition as claimed in claim 7, wherein with reference to the total composition:
the chalcogen oxyacid salt is from 1 to 10 mol%;
the titanium oxide is 50 to 98 mol%; and
the copper oxide is 1 to 40 mol%.

* * * * *